(12) United States Patent
Hennessy et al.

(10) Patent No.: US 7,482,020 B2
(45) Date of Patent: Jan. 27, 2009

(54) PROCESS FOR MAKING AN ADJUVANTED VACCINE COMPRISING HOST ALBUMIN

(76) Inventors: Kristina J. Hennessy, Bayer Corporation, 100 Bayer Rd., Pittsburgh, PA (US) 15205-9741; Karen K. Brown, Bayer Corporation, 100 Bayer Rd., Pittsburgh, PA (US) 15205-9741; Jennifer K. Lane, Bayer Corporation, 100 Bayer Rd., Pittsburgh, PA (US) 15205-9741; Sandra L. Trump, Bayer Corporation, 100 Bayer Rd., Pittsburgh, PA (US) 15205-9741

( * ) Notice: Subject to any disclaimer, the term of this patent is extended or adjusted under 35 U.S.C. 154(b) by 599 days.

(21) Appl. No.: 10/654,534

(22) Filed: Sep. 2, 2003

(65) Prior Publication Data

US 2005/0232948 A1  Oct. 20, 2005

Related U.S. Application Data

(62) Division of application No. 10/099,182, filed on Mar. 14, 2002, now Pat. No. 6,682,746, which is a division of application No. 10/015,986, filed on Dec. 12, 2001, now abandoned, which is a division of application No. 09/151,219, filed on Sep. 10, 1998, now abandoned, which is a division of application No. 08/531,820, filed on Sep. 21, 1995, now abandoned.

(51) Int. Cl.
*A61K 9/00* (2006.01)
*A61K 9/127* (2006.01)
*A61K 9/50* (2006.01)
*A61K 45/00* (2006.01)
*A61K 47/00* (2006.01)
*A61K 33/08* (2006.01)
*A01N 59/06* (2006.01)

(52) U.S. Cl. ............... 424/400; 424/499; 424/450; 424/278.1; 424/690; 424/689

(58) Field of Classification Search ........... 424/400, 424/278.1, 499, 690, 450
See application file for complete search history.

(56) References Cited

U.S. PATENT DOCUMENTS

| | | | |
|---|---|---|---|
| 3,917,819 A | 11/1975 | Yoshioka et al. ........... 424/88 |
| 4,072,565 A | 2/1978 | Weiss et al. ............ 195/1.1 |
| 4,164,565 A | 8/1979 | Prince et al. | |
| 4,582,798 A | 4/1986 | Brown et al. | |
| 4,767,622 A | 8/1988 | Ristic et al. | |
| 4,957,739 A | 9/1990 | Berget et al. | |
| 5,069,901 A | 12/1991 | Jones et al. | |
| 5,200,179 A | 4/1993 | Bordt et al. ............ 310/89 |
| 5,242,686 A * | 9/1993 | Chu et al. ............ 424/263.1 |
| 5,316,926 A | 5/1994 | Brown et al. | |
| 5,336,491 A | 8/1994 | Berget et al. | |
| 5,374,517 A | 12/1994 | Sculley et al. | |
| 5,376,369 A * | 12/1994 | Allison et al. ........... 424/278.1 |
| 5,583,014 A | 12/1996 | Brown et al. | |
| 5,911,999 A | 6/1999 | Bordt et al. ............ 310/211.1 |
| 6,682,746 B2 * | 1/2004 | Hennessy et al. ........ 424/278.1 |
| 2002/0131979 A1 * | 9/2002 | Hennessy et al. ........ 424/201.1 |
| 2005/0232948 A1 * | 10/2005 | Hennessy et al. ........ 424/202.1 |

FOREIGN PATENT DOCUMENTS

| | | |
|---|---|---|
| AU | 716702 | 3/1997 |
| CA | 2044721 | 1/1992 |
| EP | 0 066 284 | 12/1982 |
| EP | 0 074 248 | 3/1983 |
| EP | 0 310 317 | 4/1989 |
| EP | 0327305 | 8/1989 |
| EP | 0764446 A2 * | 3/1997 |
| GB | 1554446 | 10/1979 |
| WO | 85/00975 | 3/1985 |
| WO | 91/08224 | 6/1991 |
| WO | 94/14469 | 7/1994 |
| WO | 95/03826 | 2/1995 |
| WO | WO 95/12411 A1 * | 3/1995 |

OTHER PUBLICATIONS

Martin et al, Vaccine, 1988, 6/1:33-38.*
MacLean et al, Cancer Immunol. Immunother., 1993, 36:215-222.*
Goubau et al, domestic Animal Endocrinology, Oct. 1989, 6/4:339-347 abstract only.*
Rioux et al, Comparative Immunology, Microbiology and Infectious Diseases, Jan. 1997, 20/1:63-74 abstract only.*
Ben-Yedidia et al, Current Opinion in Biotechnology, 1997, 8:442-448.*
Sanchez et al, International J. Pharmaceutics, 1999, 185:255-266.*
Liu et al, FEMS immunology and Medical Microbiology, 2003, 35:141-146.*
Nesburn et al, Vaccine, 2005, 23:873-883.*
O'Bolye et al, Cancer Research, 1992, 52:5663-5667.*
Goodnough et al, ACS Symposium Series, 1994, 567:193-203.*
Goodnough et al, Applied and Environmental Microbiology, Oct. 1992, 58/10:3426-3428.*

(Continued)

*Primary Examiner*—N. M Minnifield
(74) *Attorney, Agent, or Firm*—David M. Gryte; William P. Ramey, III (57) ABSTRACT

A process for making an adjuvanted vaccine comprising host albumin. The process comprises mixing host serum or host serum with an antigen, and then mixing the resulting mixture with an adjuvant.

1 Claim, 2 Drawing Sheets

OTHER PUBLICATIONS

Naerdal et al, Clinical Allergy, 1983, 13:149-153.*

Tarelli et al, Biologicals, 1998, 26:331-346.*

Bijli et al, Clin. Exp. Allergy, 2003, 33:65-71.*

Jiang et al, J. Pharmaceutical Sciences, Oct. 2001, 90/10:1558-1569.*

Wendorf et al, J. Pharmaceutical Sciences, Dec. 2006, 95/12:2738-2750.*

Lofthouse et al, Vaccine, 2002, 20:1725-1732.*

Vijay et al, Int. Archs. Allergy Appl. Immunol., 1987, 83:325-328.*

Savolainen et al, Clinical and Experimental Allergy, 1992, 22:991-995.*

Werner, L. et al., "Immunobiological Properties of a Recombinant . . ." Molecular Immunology 28(8):819-826, 1991.

FEL-O-VAX Lv-K vaccine in the Compendium of Veterinary Products, p. 492, Third Edition, (Months unavailable) 1995-1996.

Dodds, W.J. "Vaccine Safety and Efficacy Revisited Autoimmune and Allergic Diseases on the Rise", Veterinary Forum, pp. 68-71, May 1993.

Wiedmeier, S.E. et al., "Murine Responses to Immunization with Pertussis Toxin and Bovine Serum Albumin . . ." Pediatric Research, 22(3):262-267, Sep. 1987.

Rote Liste 1994, (month unavailable), ECV, Herausgeber: Bundesverband Der Pharmazeutischen Industrie, p. 74, col. 74001-col. 74117.

Jolivet, M. "Les Adjuvants ou Comment Doper Les Vaccins et le Systeme Immunitaire", Biofutur, No. 82, Sep. 1, 1989, pp. 45-47, 50-52.

Wilde, H. et al., "Efficacy study of a new albumin-free Human Diploid Cell Rabies Vaccine (Lyssavac-HDC, Berna) in 100 severely rabies-exposed Thai patients", Vaccine, 13(6):593-596, Apr. 1995.

Pillot, J. et al. "Immunochemical Structure of the Hepatitis B Surface Antigen Vaccine—I. Treatment of Immobilized HBsAg by Dissociation Agents with or without Enzymatic Digestion and Identification of Polypeptides by Protein Blotting", Molecular Immunology, 21(1):53-60, Jan. 1984, XP002108228.

Patent Abstract of Japen, JP 63 210775 A (Doubutsuyou Seibutsugakuteki Seizai Kyokal) 1988.

Erdos, L. et al., "The demonstration of the sensitizing effect of the residual animal serum content of vaccines", Journal of Biological Standardization, 3:77-82, 1975, XP002911447.

Gottstein, B., "Purification and characterization of a specific antigen from *Echinococcus multilocularis*", Parasite Immunology, (month unavailable) 1985, 7: 201-212, XP00208229.

Purcell, R.H. et al., "Hepatitis B subunit vaccine: a preliminary report of safety and efficacy tests in chimpanzees", The American Journal of the Medical Sciences, 270(2): 395-399, Sep.-Oct. 1975, XP002108230.

Just, I. et al., "Ein Beitrag zur Stabilisierung des MVA-Impfstoffs", Zentralblatt Bakteriologies, 245(3):276-282, (month unavailable) 1979, XP002108231.

Crum, E.D. et al., "Induction of delayed-type hypersensitivity with BCG-associated proteins", Immunology, 30:497-504, (month unavailable) 1976, XP002108232.

Afeyan, N.B. et al., "Perfusion Chromatography an Approach to Purifying Biomolecules", BIO/Technology, 8:203-206, Mar. 1990, XP002108233.

Rodrigues, A.E. et al., "Bioseparations with permeable particles", Journal of Chromatography B: Biomedical Applications, 664:233-240, Feb. 3, 1995, XP004043726.

Lehman, E.D. et al., "A Novel Process for the Large-Scale Purification of Recombinant Tick Anticoagulant Peptide Using Perfusion Chromatography", BIO/Technology, 11:207-212, Feb. 1993, XP002108234.

Glad, M. et al., "New Methods for separation and recovery of biomolecules", Current Opinion in Biotechnology, 2:413-418 (month unavailable) 1991, XP002108235.

* cited by examiner

PROCESS FOR MAKING AN ADJUVANTED VACCINE COMPRISING HOST ALBUMIN

PRIORITY CLAIM TO RELATED PATENT APPLICATIONS

This application is a divisional of U.S. application Ser. No. 10/099,182, filed on Mar. 14, 2002, now U.S. Pat. No. 6,682, 746, which is a divisional of U.S. application Ser. No. 10/015, 986, filed on Dec. 12, 2001, now abandoned, which is a divisional of U.S. application Ser. No. 09/151,219, filed on Sep. 10, 1998, now abandoned, which is a divisional of U.S. application Ser. No. 08/531,820, filed on Sep. 21, 1995, now abandoned.

BACKGROUND OF THE INVENTION

1. Field of the Invention

The present invention relates to serum-based vaccines that are substantially free of non-host albumin and processes for preparing and using the same. More specifically, the present invention relates to the inventive concept of vaccines that prevent or substantially reduce post-vaccination adverse systemic reactions associated with adjuvanted vaccine regimens.

2. Brief Description of the Prior Art

It is known in the art that vaccination of animals with vaccine regimens involving the use of adjuvants can cause adverse systemic reactions. The vaccine regimen can comprise administration of inactivated vaccine containing an adjuvant. Alternately, the vaccine regimen can comprise administration of a modified live vaccine and an inactivated vaccine containing an adjuvant. Illustratively, most feline vaccine regimens comprise administration of a vaccine containing a modified live organism concomitantly with a vaccine containing an inactivated organism and an adjuvant. Associated with these vaccination regimens are adverse systemic post vaccination reactions. For instance, the use of feline leukemia vaccines (FeLV) can cause post-vaccination reactions including excess salivation, vomiting and diarrhea. See the monograph on FEL-O-VAX Lv-K® vaccine in the Compendium of Veterinary Products, page 486, Third Edition, 1995-1996. The adverse systemic reactions include anaphylaxis, hypersensitivity and atypical reactions such as vomiting and diarrhea.

Contrary to the present inventive concept, the prior art has attributed the above named systemic reactions to the presence of adjuvants, endotoxins, cellular debris residue, high concentration of modified live viruses or high antigenic mass. Dodds, *Vaccine Safety and Efficacy Revisited: Autoimmune and Allergic Diseases on the Rise*, Vet. Forum, pp 68-71, May, 1993 noted an increase in post-vaccination autoimmune and allergic diseases. Dodds has postulated that the increase is due to the immunological burden on susceptible animals exposed to a combination vaccine containing modified live organisms and adjuvanted, killed bacterins administered at the same time (as the diluent). Dodds also postulated that the immunological burden is produced by the effect of the modified live organisms.

The search for safe and effective vaccines has been limited by the paucity of information regarding the source of the problem of post-vaccination reactions. There is no indication in the literature or otherwise that teaches that these systemic reactions could be caused by an interaction of non-host albumin with an adjuvant. Indicating the contrary is the prevalent use of non-host albumin in the presence of adjuvants. Dogs receive adjuvanted rabies vaccine at the same time that they receive modified live combination vaccines containing non-host albumin. Cats receive adjuvanted FeLV vaccine in a vaccine regimen comprising the concomitant administration of a modified live vaccine containing non-host albumin. Also, combinations of albumin and adjuvants are commonly used in the art to evaluate the effectiveness of adjuvants. Albumin, generally in the form of Bovine Serum Albumin (BSA), is formulated with various adjuvants and each formulation is injected into non-bovine animals. The animals are bled at some later date and their sera are measured for antibody responses to BSA. The animals showing the best antibody responses are considered to have received the most effective adjuvants. Prince et al, U.S. Pat. No. 4,164,565 discloses the use of non-host albumin as a stabilizer in vaccines. Wiedmeier et al., Pediatric Research, Vol. 3, page 262-267, September, 1987 discloses reactivity in mice produced by immunization with *Bordetella pertussis* combined with Bovine albumin. Notably, Wiedmeier et al teaches that the cause of reactivity is the pertussis toxin in combination with albumin.

To help reduce the systemic reactions, one can purify vaccines to remove components thereof which presumably cause the systemic reactions. Animal vaccine preparations are typically purified by conventional methods such as filtration, diafiltration or centrifugation to remove components such as cells and cellular debris. Other methods of purification that yield highly purified antigens are seldom employed because they are cost prohibitive in the preparation of animal vaccines. Illustrative of the other methods of purification is column chromatography, including ion exchange chromatography, molecular sieve chromatography and hydrophobic interaction chromatography. Moreover, highly purified antigens are difficult to adjuvant with the commonly used adjuvants because they are not effective enough to stimulate a protective response with purified antigens. At any rate, these purification methods were not effective for removing non-host albumin from vaccines or precursors thereof.

The art has not attributed the cause of systemic reactions to the presence of adjuvants and non-host albumin. Certainly, the art has not attributed the cause of systemic reactions to the presence of non-host albumin in the vaccine regimen involving the use of adjuvants.

By the present invention, it has been realized that the presence of non-host albumin in an adjuvanted vaccine or vaccine regimen can cause systemic reactions. By the present invention, there is provided a novel serum-based adjuvanted vaccine or vaccine regimen that is substantially free of non-host albumin and a method of preparing the same.

SUMMARY OF THE INVENTION

In accordance with the foregoing, the present invention encompasses a serum-based vaccine comprising an immunogenically effective amount of an antigen and an adjuvant wherein said vaccine is substantially free of non-host albumin. The term "serum-based" is used herein to denote that the vaccines of the invention or their precursors employ serum including non-host serum. Typically, the serum is employed in growth media to enhance growth of organisms that are employed in the preparation of the vaccine. By the term "precursor of the vaccine" is meant vaccine components, particularly antigen, proteins other than antigen, whole organisms and harvest material. By the term "immunogenically effective amount" is meant that the antigen contains a protective component in a concentration that is sufficient to protect animals from a target disease when an adjuvanted vaccine containing the antigen is administered to animals. By the term "antigen" is meant a biological material (natural, recombinant or synthetic) that stimulates a protective immune response in animals. By the term "adjuvanted vaccine" is meant a vaccine containing an adjuvant, or a plurality of vaccines administered as a part of a vaccine regimen wherein at least one of the vaccines contains an adjuvant. By the term non-host albumin is meant albumin from the serum of an animal species other than the animal species being vaccinated. Albumin is a simple protein found in serum and has a molecular weight of about 66,000 daltons. A vaccine which is substantially free of non-host albumin contains less than 1.0 mg/mL of non-host albumin.

Also encompassed by the invention is a method of preparing the serum-based vaccine that is substantially free of non-host albumin comprising removing non-host albumin from the vaccine or a precursor thereof. An alternate method of preparing the serum-based vaccine that is substantially free of non-host albumin comprises providing a host serum containing host albumin in the preparation of the vaccine.

Further encompassed by the invention is a vaccine which is prepared by adding host serum or albumin to the vaccine antigen after harvesting or purifying the antigen from a culture of an organism from which the antigen is derived, but prior to adjuvanting the antigen. Additionally, the host serum or albumin can be added to the antigen after harvesting but prior to lyophilizing the antigen if the antigen is a modified live organism. When host serum or host albumin is used in this manner, it acts as a stabilizer. The term "stabilizer" means any additive that is added to a vaccine to prevent degradation of the antigen and the consequential loss of immunogenicity of the vaccine.

In a presently preferred embodiment of the invention, the method of preparing a serum-based vaccine containing an immunogenically effective amount of an antigen and an adjuvant wherein said vaccine is substantially free of non-host albumin comprises:

(a) growing an organism which produces the antigen in a culture containing non-host albumin;
(b) harvesting the culture;
(c) clarifying the harvest;
(d) separating the antigen and non-host albumin from the clarified harvest;
(e) separating the non-host albumin from the antigen;
(f) collecting the antigen; and
(g) formulating the antigen with an adjuvant.

In an additional preferred embodiment of the invention, the method of preparing a serum-based vaccine containing an immunogenically effective amount of an antigen and an adjuvant wherein said vaccine is substantially free of non-host albumin comprises:

(a) growing an organism which produces the antigen in a culture containing non-host albumin;
(b) harvesting the culture;
(c) clarifying the harvest;
(d) separating the antigen from the non-host albumin by passing the clarified harvest through a column with a matrix which selectively binds the antigen;
(e) washing the column matrix to remove excess non-host albumin;
(f) discarding the wash solution;
(g) washing the column matrix with a solution which elutes the antigen from the column matrix;
(h) collecting the antigen; and
(i) formulating the antigen with an adjuvant.

In another preferred embodiment of the invention, the method of preparing a serum-based vaccine containing an immunogenically effective amount of an antigen and an adjuvant wherein said vaccine is substantially free of non-host albumin comprises:

(a) growing an organism which produces the antigen in a culture containing non-host albumin;
(b) harvesting the culture;
(c) clarifying the harvest;
(d) separating the antigen from the non-host albumin by passing the clarified harvest through a column with a matrix which selectively binds the non-host albumin;
(e) collecting the antigen; and
(f) formulating the antigen with an adjuvant.

In still another preferred embodiment of the invention, the method of preparation of a serum-based vaccine containing an immunogenically effective amount of an antigen and an adjuvant wherein said vaccine is substantially free of non-host albumin comprises:

(a) growing an organism which produces the antigen in a culture containing host albumin;
(b) harvesting the culture;
(c) clarifying the harvest, if necessary; and
(d) formulating the harvest with an adjuvant.

Further encompassed by the invention is a method of eliminating adverse vaccine reactions in animals comprising administering to said animals a vaccine regimen which is substantially free of non-host albumin.

The method for eliminating adverse reactions in animals comprises administering to said animals an adjuvanted vaccine or an adjuvanted vaccine regimen which is substantially free of non-host albumin.

Also encompassed by the invention is a process for stabilizing an antigen comprising adding host serum or host albumin to said antigen prior to adjuvanting the antigen. Such a process for stabilizing an antigen can also comprise adding host serum or host albumin to said antigen prior to lyophilizing the antigen.

The vaccines of the invention are applicable for use in preventing or treating diseases of all species of animals. They are particularly suitable for use in preventing or treating diseases of companion animals such as cats, dogs and horses which are particularly sensitive to adjuvanted vaccine regimens comprising non-host albumin. In particular, the vaccines of the invention are suitable for use in preventing feline leukemia (FeLV) and rabies because they are free of problems that typically attend such vaccines. FeLV vaccines are notorious for causing adverse reactions such as hypersalivation, vomiting, diarrhea and sometimes death. Often, these reactions occur within minutes of administration of the vaccine.

Surprisingly, it has been found that animals to which the vaccines of the invention have been administered have virtually no adverse systemic reactions. The discovery that non-host albumin in a vaccine containing an adjuvant or administered in a vaccine regimen with a vaccine containing an adjuvant can cause systemic reactions is thus a part of the invention. This and other aspects of the invention are described more fully hereunder.

DETAILED DESCRIPTION OF THE INVENTION

As set forth above, the present invention encompasses a serum-based vaccine comprising an immunogenically effective amount of an antigen and an adjuvant wherein the vaccine is substantially free of non-host albumin and methods of making and using the same. It also encompasses a vaccine regimen wherein at least one vaccine in the regimen contains an adjuvant and at least one vaccine in the regimen contains non-host albumin. In addition, it encompasses a process for stabilizing an antigen comprising adding host serum or host albumin to said antigen prior to adjuvanting the antigen. Such a process for stabilizing an antigen can also comprise adding host serum or host albumin to said antigen prior to lyophilizing the antigen.

Non-host albumin is derived from non-host serum that is typically used in growing organisms from which the antigens are derived. Typical examples of non-host serum (containing non-host albumin) can be selected from the group consisting of bovine serum, fetal bovine serum, equine serum, fetal equine serum, sheep serum and goat serum. On the other hand, if equine albumin is present in an equine vaccine, the vaccine is considered to contain host albumin.

The antigen is obtained from an organism selected from the group consisting of bacteria, virus, parasite, rickettsia and protozoa. Examples of the bacteria can be selected from the group consisting of *Bordetella* spp., *Streptococcus* spp., *Staphylococcus* spp., *Clostridium* spp., *Leptospira* spp., *Escherichia* spp., *Salmonella* spp., *Pasteurella* spp., *Mycobacteria* spp., *Mycoplasma* spp., *Moraxella* spp., *Haemophilus* spp., *Borrelia* spp., *Fusobacteria* spp., *Bacteriodes* spp. and *Rhodococcus* spp. Examples of the viruses can be selected from the group consisting of herpes viruses, parainfluenza viruses, reoviruses, rotaviruses, morbilliviruses, retroviruses, coronaviruses, adenoviruses, togaviruses, parvoviruses, parapox viruses, paramyxoviruses, cytomegaloviruses, arboviruses and hantaviruses. More specifically, such viruses would include but not be limited to feline leukemia virus, feline rhinotracheitis, feline calicivirus, feline panleukopenia virus, feline immunodeficiency virus, feline infectious peritonitis virus, canine hepatitis, canine adenovirus type 2, canine parvovirus, rabies virus, canine parainfluenza virus, canine coronavirus, equine herpes viruses, equine influenza viruses and equine encephalomyelitis viruses. Examples of parasites and protozoa can be selected from the group consisting of *Neospora* spp., *Toxoplasma* spp., *Dirofilaria* spp., *Cryptosporidium* spp., *Giardia* spp., *Babesia* spp. and *Coccidia* spp. An example of *rickettsia* can be selected from the group consisting of *Chlamydia* spp., Potomac Horse Fever, *Ehrlichia canis*, and other *Ehrlichia* spp.

The antigens can be obtained from a member selected from the group consisting of: a whole culture of an organism such as a whole culture harvest, a partially purified whole culture harvest, a purified subunit extracted from harvest, a subunit obtained via recombinant technology and expressed in the homologous or a heterologous organism, a deletion mutant of the whole organism (conventional or rDNA gene-deleted mutants), peptides, naked DNA, chemically synthesized antigens, reverse transcribed naked cDNA or combinations thereof.

Generally, the antigen can be produced by art-known techniques of culturing and harvesting organisms, concentrating and/or conventionally purifying antigens of such organisms. For example, the antigen can be produced by: growing the selected organism in a culture having growth medium containing a non-host serum (serum-based culture). More specifically, the organism can be grown in a tissue culture prepared from mammalian or plant cells wherein non-host serum is added to the medium to enhance the growth of the organism. The organism can also, be grown in fermentation media wherein the organism grows without tissue culture but has added thereto a growth medium containing a non-host serum. Typically, the non-host serum can be selected from the group consisting of fetal bovine serum, bovine serum, calf serum, fetal equine serum, horse serum, goat serum, lamb serum and sheep serum. At the completion of growth, the culture is harvested and, if necessary, conventionally purified by, say, filtration and/or ultrafiltration to remove cells, cellular debris and extraneous contaminants. However, these techniques do not remove the non-host albumin. At this point, the culture harvest still contains non-host albumin and would not be acceptable if combined with adjuvant and/or administered in a regimen with an adjuvanted vaccine. Therefore, the resulting culture harvest is further purified in accordance with this invention to remove the non-host albumin prior to its formulation into an adjuvanted vaccine.

In accordance with the invention, the non-host albumin can be removed by a process of purifying the vaccine or a precursor of the vaccine in such a manner as would remove the non-host albumin. The process of purifying the precursor of the vaccine can be done by a chromatography technique selected from the group consisting of PERFUSION CHROMATOGRAPHY® (PerSeptive Biosystems), ion exchange chromatography, molecular sieve chromatography, hydrophobic interaction chromatography, affinity chromatography and combinations thereof. Preferably, the process of purification is by PERFUSION CHROMATOGRAPHY® using hydrophobic interaction chromatography matrices or a combination of hydrophobic interaction chromatography and ion exchange chromatography. The following is an illustrative but non-limiting description of the hydrophobic interaction chromatography with a PERFUSION CHROMATOGRAPHY® matrix utilizing POROS® media (PerSeptive Biosystems).

PERFUSION CHROMATOGRAPHY® is carried out using a matrix (POROS® media) having large channeled pores which carry molecules swiftly into the interior of each bead by convective flow as well as diffusive pores that branch off the channeled pores providing a large internal surface area for binding. This pore combination provides high capacity, high resolution and high speed purification. Hydrophobic interaction chromatography involves the use of polar groups on an uncharged matrix to interact with polar residues (e.g. phenylalanine) on proteins, causing retardation and separation of proteins based on their relative hydrophobicities. The use of the POROS® media matrix allows much greater flow rates at higher pressures so that the purification time is reduced, thus reducing the cost and allowing chromatography to be cost effective for veterinary products.

Hydrophobic interaction chromatography is performed by adding a high ionic strength buffer to fluids of the culture harvest containing the non-host albumin before adding such fluids to the hydrophobic column. The column is washed several times with a high ionic strength buffer such as 20 millimolar (Mm) sodium phosphate/650 Mm sodium sulfate before addition of the high ionic strength buffered fluids of the culture harvest containing the non-host albumin (column feed material). Multiple column volumes of column feed material are run through the column. The column matrix binds both the non-host albumin and the antigen (contained within the buffered fluids of the culture harvest). To elute non-host albumin from the column, the column is washed multiple times with a high ionic strength buffer such as 20 Mm sodium phosphate/650 Mm sodium sulfate or until the optical density reading at a wavelength of 280 nanometers (nm) of the eluate is less than 0.03. The antigen (purified) is eluted from the column by washing the column matrix with multiple volumes of a low ionic strength solution which can be sterile water. The purified antigen is collected in a separate collecting vessel when the optical density of the eluate increases above 0.15. Collection of the eluate ceases when the optical density of the eluate drops below 0.10.

Another method for removal of non-host albumin according to this invention encompasses use of affinity chromatography for binding of either the antigen or the non-host albumin. For instance, the antigen can be produced by art-known techniques of culturing and harvesting organisms and clarifying, concentrating and/or conventionally purifying, antigens of such organisms as described previously. For removal of the non-host albumin the clarified harvest can be added to a column containing a matrix which binds either the antigen or which binds the non-host albumin. Such a matrix could be a lectin such as CIBACRON BLUE™ (Pharmacia) or MIMETIC BLUE® (Affinity Chromatography Ltd.), both of which bind non-host albumin, or a matrix which contains a polyclonal or monoclonal antibody specific for the antigen or non-host albumin, whichever is to be bound to the matrix. The clarified harvest becomes the column feed material and is added to the column. If the column contains a matrix such as a lectin, a polyclonal antibody or a monoclonal antibody specific for non-host albumin, the non-host albumin is bound to the column and the antigen passes through the column and is collected. The collected antigen is then formulated with adjuvant to prepare a vaccine. If the column contains a matrix such as a polyclonal antibody or monoclonal antibody specific for antigen, the clarified harvest material is added to the column and the antigen is bound to the matrix. The non-host albumin passes through the column and is discarded. Excess non-host albumin is removed from the column matrix by washing with a buffer which does not remove the antigen. Then the matrix is washed with a solution which elutes the antigen from the column matrix. Such washing and elution buffers can be based on pH, ionic strength or polarity differences of the antigen to be eluted. The antigen is then collected and formulated with an adjuvant to produce the vaccine. If a lectin is used to bind non-host albumin, the antigen which is collected will have to be further purified through a second lectin column or by using another type of chromatography to remove all of the non-host albumin.

If one has a whole organism such as a virus or bacteria or a very large antigen, for instance, one with a molecular weight greater than 100,000 daltons, molecular sieve chromatography can be used to separate the antigen from the non-host albumin which has a molecular weight of only about 66,000 daltons. Molecular sieve chromatography separates molecules on the basis of molecular weight. The matrix is selected so that low molecular weight molecules such as non-host albumin pass through the column at a faster rate than large molecular weight molecules such as large antigens. Using this technique, the organism is grown in a culture containing non-host albumin and harvested, clarified and/or concentrated and purified by conventional techniques as described previously. In order to separate the non-host albumin from, for instance, a whole virus, the virus is grown in tissue culture, harvested by collecting the fluids from the tissue culture and clarified to remove the cellular debris. This clarified harvest is the column feed material and is added to the column. The first fluid to pass through the column is collected and discarded since it contains the non-host albumin. The virus passes through the column slower and can be washed into a collection vessel using buffers which do not harm the virus. Virus which has been collected in this manner can be formulated with an adjuvant to prepare a vaccine.

An alternate method of preparing the serum-based vaccine containing an immunogenically effective amount of an antigen and an adjuvant wherein said vaccine is substantially free of non-host albumin comprises culturing the organism in host serum wherein there is no non-host albumin. By this method, one grows the organism in tissue culture or fermentation media containing host serum instead of non-host serum. Conventional harvesting, concentration and purification can be used if a pure product is desired. No further purification to remove non-host albumin is required because the preparation does not contain non-host albumin. By this method, the crude harvest material can also be used to formulate the vaccine. Using this method the harvest material can simply be combined with adjuvant to formulate the vaccine.

Following the purification and/or removal of the non-host albumin or growth of the organism in host serum, the antigen is inactivated and adjuvanted by conventional techniques. Generally stated, the antigen can be inactivated by treating it with an inactivating agent which does not denature the protective component of the antigen. Specifically, the antigen can be inactivated by treating it chemically, by irradiation, by heating or by freeze-thaw. Illustratively, one can employ chemical inactivating agents selected from the group consisting of formalin, beta-propiolactone, detergents and binary ethyleneimine. Different ones of these chemical inactivating agents are preferred for different organisms.

The inactivated antigen can also be concentrated or pooled with other harvested antigen prior to adjuvanting. The amount of concentration would be such that the average amount of antigen or Relative Potency (RP) value meets or exceeds the minimum acceptable value for a vaccine. The inactivated antigen may be concentrated up to 100 fold, if necessary, by ultrafiltration with a molecular weight cut-off which will suitably maintain the antigen and allow contaminants to pass through and be discarded or by differential centrifugation. After inactivation, the antigen value must be above the acceptable minimum level or RP. Then it is stored at temperatures from −70° C. to +10° C. until it is mixed or microfluidized with an adjuvant.

The inactivated antigen is formulated or combined with an adjuvant. Adjuvants are chemicals or bacterial or virus-derived components added to vaccines to enhance the production of an immune response by the animal receiving the vaccine. Adjuvants fall into the general categories of polymers, block co-polymers, oils, oil-in-water, aluminum salts, and bacterial and viral extracts. Most adjuvants function by producing an irritation at the site of injection causing leukocytes (immune cells) to infiltrate the area and/or by producing a depot effect (holding the antigens at the injection site for as long as possible). Some of the newer adjuvants act as slow-release mechanisms, releasing antigens encapsulated by them at a relatively slow rate. Even newer adjuvants directly affect the B-cells or T-cells of the immune system and are called immune stimulators, immune regulators, immune modulators or immune enhancers. If an adjuvant causes extensive infiltration of leukocytes to the injection site, swelling and injection-site reactions will occur. The immune response to adjuvants may also enhance the reactivity to contaminants such as endotoxins, thereby increasing the probability of systemic reactions such as anaphylaxis. Therefore, although adjuvants are necessary for stimulation of the immune response by inactivated vaccines, they can produce detrimental side effects. The adjuvant is selected from the group consisting of polymers, block co-polymers, oils, oil-in-water, water-in-oil, aluminum salts, immuno-modulators and combinations thereof. Preferably, the adjuvant is a polymer or block co-polymer. The adjuvant can be employed in an amount of from 0.01% to 50%. The amount of adjuvant is strictly correlated to the type of adjuvant used. However, it is important that the adjuvant be employed in an effective amount to immunogenically stimulate the inactivated antigens. When used in such an amount, adjuvants can stimulate adverse reactions to non-host albumin.

After inactivating and adjuvanting the antigen, the potency or Relative Potency (RP) of the antigen can be adjusted to an appropriate level which meets or exceeds the minimum acceptable amount of antigen to produce an immunogenically effective vaccine. The tests used for such potency or relative potency testing are described hereunder. The antigen(s) can be formulated with other antigens. For example, inactivated and adjuvanted feline leukemia virus prepared in accordance with the invention can be formulated with feline calicivirus, feline panleukopenia virus, feline rhinotracheitis virus and feline chlamydia. Additionally, inactivated and adjuvanted rabies virus prepared in accordance with the invention can be formulated with canine parvovirus, canine distemper virus, canine parainfluenza virus, canine adenovirus type 2 and various *Leptospira* spp. Also, inactivated and adjuvanted equine viruses and bacterial antigens can be prepared in accordance with the invention. Some or all of these additional antigens may be prepared according to the present invention. Some of the additional antigens may be modified live. However, the final combination vaccines will be substantially free of non-host albumin if the combination vaccine or vaccine regimen wherein the combination vaccine is administered contains an adjuvant. The resulting adjuvanted vaccine that is substantially free of non-host albumin is safe and effective and can be administered to animals with essentially no post-vaccination, adverse systemic reactions.

As a measure of vaccine potency that equates to vaccine protection in the host animal, each individual lot of antigen (crude or purified) and serial of vaccine undergoes testing. The measurement may involve vaccination of laboratory animals or host animals followed by a challenge of the animals, vaccination of laboratory animals or host animals followed by evaluation of a serological response or the performance of an Enzyme Linked Immunosorbant Assay (ELISA) to measure the amount of antigens in the vaccine. An Enzyme Linked Immunosorbant Assay (ELISA) is preferable as it eliminates animal testing. In the latter method, the antigen concentration in the test vaccine is measured against the antigen content in a Reference Vaccine which has been proven to be protective in the host animal. A test vaccine which measures 1.0 as compared with the Reference Vaccine is considered to be potent and is said to have a relative potency (RP) of 1.0. The RP can be measured before or after the antigen has been harvested, purified, inactivated or adjuvanted. Before inactivation and adjuvanting, the RP must be above 1.0 so that after inactivation and adjuvanting it does not fall below 1.0.

The purified antigen in accordance with the invention, may be concentrated or pooled with other purified harvested antigen such that the average amount of antigen meets or exceeds the minimum acceptable value for a harvest. The purified antigen may be concentrated up to 100 fold, if necessary, by ultrafiltration with a molecular weight cut-off which will suitably maintain the antigen and allow contaminants to pass through and be discarded or by differential centrifugation. It is important to note that even if very low levels of serum are used for growth enhancement, it is virtually impossible to remove its albumin content from cultures of the organism or vaccines by conventional purification processes, especially if concentration is used. For instance, if antigen is concentrated 100 fold, a non-host albumin level of 0.1% (1 mg/mL) in the antigen prior to concentration would be concentrated to 10% or 100 mg/mL after concentration. Such a level would be totally unacceptable in the final vaccine.

As would be realized from the foregoing, a distinct feature of the invention is the discovery of the source of the problem of post-vaccination adverse systemic reactions and the solutions for the problem. Without being bound to any particular theory, it is believed that the adverse post-vaccination systemic reactions result from the presence of adjuvants and non-host albumin in vaccines or vaccine regimens. There is hereby discovered and disclosed a solution which includes removing non-host albumin from vaccines which contain an adjuvant or which are administered in vaccine regimens which contain adjuvanted vaccines or using host serum for antigen preparation in place of non-host serum and administering vaccines and vaccine regimens which are substantially free of the non-host albumin.

These and other aspects of the invention are further illustrated by the following non-limiting examples. In the examples and throughout the specification, parts are by weight unless otherwise indicated.

EXAMPLES

Example 1

Figure 1:
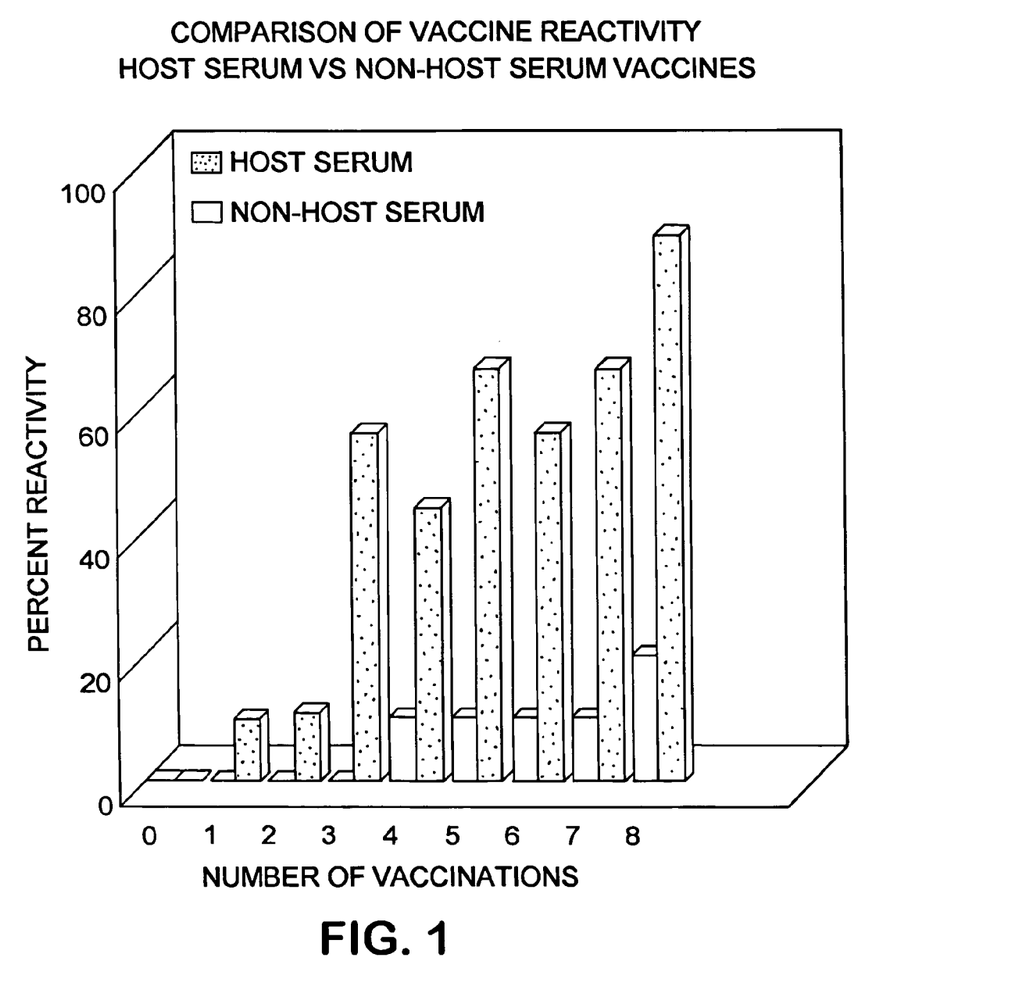
FIG. 1 is a graph presenting a comparison of the reactivity of a vaccine containing an adjuvant combined with non-host albumin with the lack of reactivity of a vaccine containing an adjuvant in combination with host albumin.

In order to evaluate whether there was a difference in reactivity of equine vaccines prepared with non-host serum (fetal bovine serum as the conventional approach) or equine vaccines prepared with host serum (fetal equine serum) two mock vaccines were prepared. One vaccine contained adjuvanted media with 15% fetal bovine serum (non-host serum approach) while the second vaccine contained 15% fetal equine serum (host serum). Twenty horses were used for this study. The adjuvant in the two approaches was from the same lot of material and was a CARBOPOL® based adjuvant. Ten horses each received a 2.0 mL dose of the fetal bovine serum-containing mock vaccine injected intramuscularly in the neck and each of an additional ten horses received a 2.0 mL dose of the fetal equine serum-containing mock vaccine injected intramuscularly in the neck. A booster injection of the respective vaccines was administered every 28 days over approximately 8 months. The horses were observed for reactions on days 1, 2, 3, 4, 7 and 14 following each injection. Just before the second injection, one of the horses receiving the fetal bovine serum preparation died of contortion of the intestine. The remaining 9 horses received a booster injection and were observed after booster doses of the fetal bovine serum-containing mock vaccine. The results of these observations are shown in FIG. 1.

Following administration of all injections of the fetal equine serum-containing mock vaccine, there were no systemic reactions (0 out of a possible 480 observations). Only 2 out of a possible 480 instances of swelling of 4" or greater in diameter were observed. The swelling occurred in 2 consecutive observations of the same horse after receiving 4 injections. Swelling of 1-3" in a diameter was observed in 3 out of a possible 480 observations. Thirty one (31) reactions of any type were observed out of a possible 480 observations. All reactions occurred in only 1 of the 10 horses (10%) through vaccination # 8 after which 2 of the 10 horses showed a local reaction. Comparatively, following administration of all injections of the fetal bovine serum mock vaccine, there was one possible systemic reaction (the death of horse #606). Severe swelling (larger than 4" in a diameter) was observed in 22 out of a possible 432 observations. Visible swelling (1-3" in a diameter) was observed in 34 out of a possible 432 observations. One hundred and forty-six (146) reactions were noted out of a possible 432 observations. Eight of the remaining 9 horses (89%) showed reactivity by vaccination # 8 with 5 of 9 horses reacting routinely after each vaccination. These data indicate that in repeat injection with adjuvanted vaccines, the presence of non-host serum (fetal bovine serum in equine vaccines) causes considerably more reaction than the presence of host serum (fetal equine serum).

Example 2A

CRFK cells (Crandell Feline Kidney) persistently infected with FeLV were grown to 95% confluency as follows. The cells were grown in 850 cm2 roller bottles incubated with rotation at 37° C. Employed as the growth medium was Dulbecco's Minimal Essential Medium with high glucose levels (DMEM-Hi) containing 10% fetal bovine serum and 30 ug/ml neomycin. After the cells reached confluency, the media was changed to maintenance media (DMEM-Hi media containing 5% fetal bovine serum). After four days this media was decanted and viral fluids were harvested. Cells were re-fed with maintenance media and viral fluids were collected every three to four drays for a total of seven harvests. Decanted viral fluids from each harvest were tested for sterility, aliquoted into sterile plastic containers and stored frozen at −70° C. Upon satisfactory sterility testing, viral fluids were thawed at room temperature and pooled into a single sterile receiving vessel. Viral fluids were clarified through a 3 micron polypropylene filter to remove cell debris and then concentrated 10-fold using a 30,000 dalton molecular weight cut-off tangential flow ultrafiltration device. Fluids were then washed in 50 Mm $Na_2HPO_4$ to a 9-fold final concentration factor. The pooled concentrate had a total protein content of 16.59 mg/mL.

A cation exchange chromatography column was initially used to purify the virus and its subunits from the remainder of the fluids. A one-liter, 14 cm×10 cm column was packed with Q SEPHAROSE® chromatography resin (Pharmacia) and sanitized with two column volumes of 1 M NaOH. In addition, the column accessories such as pumps, tubing and fittings to the column were sanitized with 1 M NaOH. The column and all accessories were then rinsed with a 50 mM $Na_2HPO_4$ (pH 7.0) buffer until the effluent from the column was at pH 7.0. All buffers were 0.2 µm filter sterilized before use. A BIOPILOT® chromatography system (Pharmacia) was the hardware used for this entire process.

A 1500 mL sample of the FeLV concentrated viral fluids (column feed material) was injected onto the column. The column was washed with 9 column volumes of Buffer A (50 mM $Na_2HPO_4$) at 80 mL/min before elution of the virus with a linear gradient of Buffer B (50 mM $Na_2HPO_4$, 1 M NaCl) from 0% to 50% Buffer B within 10 column volumes. A final elution of residual virus was accomplished with 5 column volumes of 100% Buffer B. Fractions eluted from the column were collected and examined for total protein content. The total protein content was 3.12 mg/mL. Approximately half of this would be non-host albumin. Fractions containing the virus were then pooled and rechromatographed over a hydrophobic interaction column to remove the remainder of the non-host albumin content.

Ammonium sulfate was added to the eluted virus fractions from the Q SEPHAROSE® column (which still contained >1 mg/mL of non-host albumin) to achieve a final concentration of 0.5 M. This virus fraction column feed material was loaded onto a 1 liter phenyl sepharose low substitution hydrophobic interaction column that had been previously equilibrated with 50 mM $Na_2HPO_4$. The column was washed with a combination of 50 mM $Na_2HPO_4$ and 0.5 M $(NH_4)_2SO_4$ for 5 column volumes. The virus was then eluted from the column with a 50 mM $Na_2HPO_4$ buffer. Virus fractions eluted from the column were tested for sterility, total protein and non-host albumin content. All virus fractions were sterile, the total protein content was between 0.9 and 1.2 mg/mL and the non-host albumin content was below 0.5 mg/mL. The viral fraction (fluids) was inactivated with 0.03% formalin and formulated into vaccines by combining with either 5% POLYGEN™ adjuvant (obtained from MVP Laboratories, Ralston, Nebr.), 0.25% glycerol/EDTA stabilizer and 30 ug/mL nystatin (FLV011) or 0.125% CARBOPOL® adjuvant, 0.25% glycerol/EDTA stabilizer and 30 ug/mL nystatin (FLV09).

Ten to twelve week old cats were immunized with a one mL dose of vaccine subcutaneously. Three weeks later the cats were given a one mL booster immunization. Cats were challenged ten days post booster vaccination with virulent feline leukemia virus. This challenge was conducted as follows: 1) cats were immunosuppressed with 10 mg/kg body weight of methylprednisolone acetate intramuscularly for two successive days; and 2) cats were challenged with approximately $1.5 \times 10^6$ focus forming unit (FFU) of virulent feline leukemia virus intranasally on each day of immunosuppression. Cats were checked at day 15 and day 1 prior to challenge exposure to make sure that they were not already infected with FeLV or were not carriers. Beginning three weeks after challenge, blood was collected from cats for nine successive weeks and examined for "p27e" antigen by an indirect immunofluorescence assay. All results of the vaccinates and control cats are presented in Table 1. A positive test result for a cat was defined as three consecutive weeks of viremia or five weeks of viremia during the twelve week period. The results indicate that 100% of the cats vaccinated with "FLV011" vaccine and seventy percent of the cats vaccinated with "FLV009" vaccine were protected from challenge, whereas, 81 percent of control cats were infected by the challenge dose. This is equal to or better than the protection provided by conventionally-produced but reactive commercial FeLV vaccines which protect from 15 to 80 percent of the vaccinated cats in a similarly intense challenge. This FLV009 vaccine serial became the Standard Reference for future ELISA assays and, by definition, contains an RP of 1.0.

TABLE 1

FELINE LEUKEMIA VIRUS VACCINATION/CHALLENGE STUDY - DETECTION OF PERSISTENT VIREMIA BY MEASUREMENT OF p27

| Test Grp. | CAT NO. | D-15 | D-1 | D-34 | Wk 3 | Wk 4 | Wk 5 | Wk 6 | Wk 7 | Wk 8 | Wk 9 | Wk 10 | Wk 11 | Wk 12 |
|---|---|---|---|---|---|---|---|---|---|---|---|---|---|---|
| FLV 009 | VL2 | − | − | − | − | − | − | − | − | − | − | − | − | − |
|  | VM3 | − | − | − | − | − | − | − | − | − | − | − | − | − |
|  | VQ2 | − | − | − | − | − | − | − | − | − | − | − | − | − |
|  | VV4 | − | − | − | − | − | − | − | − | − | − | − | − | − |
|  | VX2 | − | − | − | + | + | + | + | + | + | + | + | + | + |
|  | WC1 | − | − | − | − | − | − | − | − | − | − | − | − | − |

TABLE 1-continued

FELINE LEUKEMIA VIRUS VACCINATION/CHALLENGE STUDY -
DETECTION OF PERSISTENT VIREMIA BY MEASUREMENT OF p27

| Test Grp. | CAT NO. | D-15 | D-1 | D-34 | Wk 3 | Wk 4 | Wk 5 | Wk 6 | Wk 7 | Wk 8 | Wk 9 | Wk 10 | Wk 11 | Wk 12 |
|---|---|---|---|---|---|---|---|---|---|---|---|---|---|---|
| | WE3 | − | − | − | + | + | + | + | + | + | + | + | + | + |
| | WF6 | − | − | − | − | − | − | − | − | − | − | − | − | − |
| | WH5 | − | − | − | − | − | − | − | − | − | − | − | − | − |
| | WK3 | − | − | − | + | + | + | + | + | + | + | − | − | − |
| FLV 011 | VL5 | − | − | − | − | − | − | − | − | − | − | − | − | − |
| | VN1 | − | − | − | − | − | − | − | − | − | − | − | − | − |
| | VW3 | − | − | − | − | − | − | − | − | − | − | − | − | − |
| | VY4 | − | − | − | − | − | − | − | − | − | − | − | − | − |
| | WD2 | − | − | − | − | − | − | − | − | − | − | − | − | − |
| | WF1 | − | − | − | − | − | − | − | − | − | − | − | − | − |
| | WG3 | − | − | − | − | − | − | − | − | − | − | − | − | − |
| | WJ4 | − | − | − | − | − | − | − | − | − | − | − | − | − |
| | WL5 | − | − | − | − | − | − | − | − | − | − | − | − | − |
| | VT5 | − | − | − | − | − | − | − | − | − | − | − | − | − |
| Cont | VL1 | − | − | − | − | − | − | − | − | − | − | − | − | − |
| | VM2 | − | − | − | + | + | + | + | + | + | + | + | + | + |
| | VQ1 | − | − | − | − | − | − | − | − | − | − | − | − | − |
| | VV3 | − | − | − | + | + | + | + | + | + | + | + | + | + |
| | VX1 | − | − | − | + | + | + | + | + | + | + | + | + | + |
| | WB | − | − | − | + | + | + | + | + | + | + | + | + | + |
| | WE2 | − | − | − | + | + | + | + | + | + | + | + | + | + |
| | WF3 | − | − | − | + | + | + | + | + | + | + | + | + | + |
| | WH4 | − | − | − | + | + | + | + | + | + | + | + | + | + |
| | WJ6 | − | − | − | + | + | + | + | + | + | + | + | + | + |
| | WM | − | − | − | + | + | + | + | + | + | + | + | + | + |

Cont = CONTROLS, D = DAY, WK = WEEK POST CHALLENGE
D-34 = The Day of Challenge
Data reported as Indirect Fluorescent Antibody (IFA) results.

Example 2B

The vaccine of EXAMPLE 2A was evaluated for safety by 21 practicing veterinarians in clinical field trials conducted in five states. A total of 913 doses of vaccine were administered to 850 cats between 8 weeks and 15 years of age. The veterinarians were requested to specifically note any systemic reactions and record the circumstances surrounding such incidences should they occur. Only one systemic reaction was noted. This reaction occurred in a cat which received a concomitant modified live feline combination vaccine which contained non-host albumin. Therefore, it is concluded that the FeLV vaccine was safe and that systemic vaccine reactivity can be eliminated by administering vaccines which do not contain a combination of non-host albumin and an adjuvant whether administered in the same vaccine or whether administered in a concomitant vaccine as part of a vaccination regimen.

Example 3

CRFK cells persistently infected with FeLV were grown to 95% confluency in DMEM-Hi containing 10% fetal bovine serum and 30 ug/ml neomycin using 850 cm$^2$ roller bottles incubated with rotation at 37° C. as in EXAMPLE 2A. After the cells reached confluency, the media was changed to maintenance media (DMEM-Hi media containing 5% fetal bovine serum). After four days, this media was decanted and viral fluids were harvested. Cells were refed with maintenance media and viral fluids were collected every three to four days for a total of seven harvests. Decanted viral fluids from each harvest were tested for sterility. All harvest fluids were found to be sterile. Viral fluids from each harvest were aliquoted into sterile plastic containers and stored frozen at −70° C. Upon satisfactory sterility testing, viral fluids were thawed at room temperature and pooled into a single sterile receiving vessel. The total protein content of this pooled FeLV was 2.5 mg/mL. Viral fluids were clarified through a 5 micron and a 1 micron polypropylene filter to remove cell debris.

Clarified viral fluids (harvest fluid column feed material) were purified to remove non-host albumin by using a purification technique comprising PERFUSION CHROMATOGRAPHY® using a hydrophobic interaction chromatography matrix. The matrix used was obtained from PerSeptive Biosystems and was their POROS® PE 50 media. This technique uses polar groups on an uncharged matrix to interact with polar residues (e.g. phenylalanine) on proteins, causing retardation and separation of proteins based on their relative hydrophobicities. This interaction was enhanced by adding high ionic strength sodium sulfate/sodium phosphate to the viral fluids before adding them to the hydrophobic column. The column was washed with three column volumes of a buffer containing 20 mM sodium phosphate, 650 mM sodium sulfate before addition of harvest fluid column feed material. The equivalent of five column volumes of harvest fluid column feed material (before dilution with sodium sulfate/-sodium phosphate) was then run through the column. To elute non-host albumin from the column, the column was washed with five column volumes of 20 mM sodium phosphate/650 mM sodium sulfate or until the optical density reading of the eluate was <0.03 at a wavelength of 280 nm. Resultant purified viral components were eluted from the column by washing the column resin with five column volumes of sterile water. Purified viral fractions were collected in a separate collecting vessel when the optical density (at 280 nm) of the eluate increased above 0.15 and collection of the eluate ceased when the optical density of the eluate dropped below 0.10.

Figure 2:
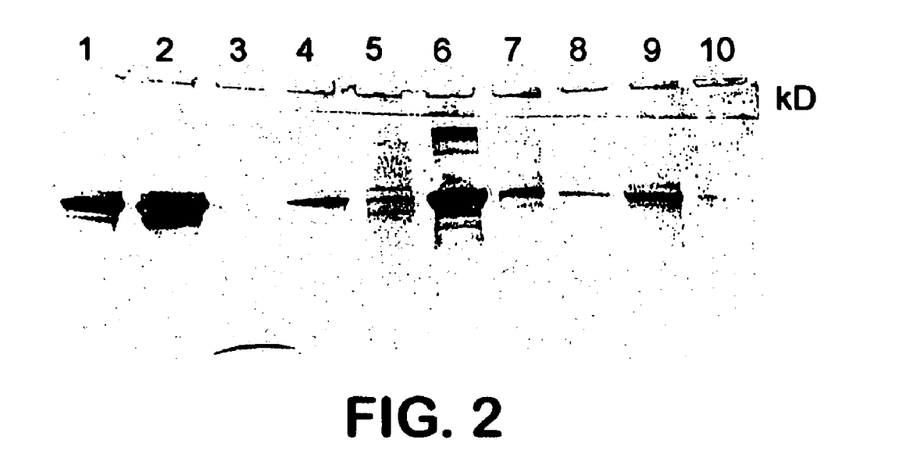
FIG. 2 is a photograph of a SDS-PAGE gel comparing 9 different feline vaccines wherein the non-host albumin content is shown.

Purified viral fluids were tested quantitatively for total protein content and qualitatively by SDS-PAGE for non-host albumin content. The total protein was 1.35 mg/mL and the non-host albumin content was less than 0.5 mg/mL. To remove excess salts which are retained by the purified virus fluids, these fluids were diafiltered with ten volumes of Dulbecco's phosphate buffered saline using a 30,000 dalton molecular weight cut-off tangential flow ultrafiltration device. Fluids were concentrated at this time to achieve a sufficient final concentration of FeLV gp70 to batch vaccine. Viral fluids were inactivated with 0.03% formalin for 72 hours at 4° C.

A feline leukemia vaccine was produced from purified, inactivated viral fluids by addition of 0.125 mg/ml CARBOPOL®, 0.25% glycerol/EDTA and 30 ug/ml nystatin to the inactivated viral fluids at a sufficient concentration to be immunogenically effective when combined with the adjuvant. This vaccine was compared to the vaccine in EXAMPLE 2A using an ELISA (Enzyme Linked Immunosorbant Assay) to measure potency (immunogenic effectiveness). This ELISA measures the amount of antigenic component in the FeLV vaccine as compared with a Standard Reference. The Standard Reference is the vaccine described in EXAMPLES 2A and 2B (FLV 009), which has been demonstrated to protect cats in a vaccination/challenge study. A result of 1.00 in the ELISA indicates that the amount of FeLV protective antigen component in the vaccine being tested is equivalent to that of the vaccine of EXAMPLES 2A and 2B and will protect cats equally well. The vaccine of this example demonstrated a potency of 1.32. It contained a protein content of 1.1 mg/mL with no detectable non-host albumin.

It is thus demonstrated that passage of FeLV harvest material containing non-host albumin through a hydrophobic matrix alone can remove the albumin and be used to produce an immunogenically effective vaccine.

Example 4

Six mock vaccines were formulated containing only 5% bovine fraction V albumin (non-host albumin) diluted in phosphate buffered saline and combined with different adjuvants. The vaccine formulations were administered to fifty eight (58) cats of approximately 22-26 weeks of age that had previously received two doses of a combination killed rhinotracheitis virus-calicivirus-panleukopenia virus vaccine that contained serum proteins from tissue culture components. The cats had also been vaccinated with a purified feline leukemia vaccine containing no detectable non-host albumin. Cats were randomly assigned to an non-host albumin/adjuvant vaccine group and were immunized with a 1.0 mL dose of vaccine weekly for 3 successive weeks. Daily observations were made for evaluation of reactivity. Results of these observations are shown in TABLE 2. Approximately six hours after the first weekly vaccination, two cats showed clinical signs of systemic reactions. The vaccinations given to these cats were of two different non-host albumin/-adjuvant formulations. Clinical signs included weakness and incoordination, vocalization, blood-tinged frothy vomiting, cyanotic extremities, pale mucous membranes with delayed capillary refill time (3.5 seconds), hypersalivation and hyperpnea. Treatment with dexamethasone and subcutaneous fluids did little to relieve symptoms. These two cats were subsequently euthanized.

Approximately four hours after the second weekly injection, one additional cat demonstrated more moderate signs of a systemic reaction to vaccination. Clinical signs associated with this animal included lethargy, red mucous membranes, cyanotic/reddened pinna and swollen eyes. This experiment proves that the unusual reactivity commonly associated with FeLV vaccines (vomiting and diarrhea) can be reproduced by a combination of non-host albumin with an adjuvant. The reaction rate which was demonstrated in this experiment appears low. However, in the clinical situation, such reactions are only seen in less than 1.0% of cats. This experiment demonstrated a 2.0% reaction rate if all cats are included in the calculation.

TABLE 2

DEMONSTRATION THAT NON-HOST ALBUMIN IN COMBINATION WITH ADJUVANTS PRODUCES SYSTEMIC REACTIONS IN ANIMALS

| VACCINE NUMBER | ADJUVANT | AMT. OF ADJUVANT | NO. OF REACTIONS/ NO. OF CATS WK 1 | WK 2 | WK 3 |
|---|---|---|---|---|---|
| 1 | NONE | N/A | 0/8 | 0/8 | 0/8 |
| 2 | ADJUVANT B | 50% | 0/12 | 1/12 | 0/12 |
| 3 | CARBOPOL ® | 0.125 mg/mL | 1/8* | 0/7 | 0/7 |
| 4 | CARBOPOL ® | 0.25 mg/mL | 0/6 | 0/6 | 0/6 |
| 5 | ALUMINUM HYDROXIDE | 10% | 0/8 | 0/8 | 0/8 |
| 6 | EMULSIGEN ® | 5% | 0/8 | 0/8 | 0/8 |
| 7 | POLYGEN ™ | 5% | 1/8* | 0/7 | 0/7 |

*INDICATES THAT THE CAT WAS EUTHANIZED DUE TO THE SEVERITY OF THE REACTION

Example 5

Combination five-way feline vaccines prepared from modified live or inactivated feline rhinotracheitis, feline calicivirus, feline panleukopenia, feline chlamydia and feline leukemia virus are known in the art and are also associated with the reactivity described previously. A combination inactivated feline rhinotracheitis, feline calicivirus, feline panleukopenia, feline chlamydia and feline leukemia vaccine was prepared according to this invention. The feline rhinotracheitis virus, feline calicivirus, feline panleukopenia virus and feline chlamydia virus protective antigen components were grown individually in tissue culture without the use of serum or albumin. The protective antigen components were harvested and all contained cell debris. The individual harvest fluids were clarified through 3 μm filters, inactivated individually with 0.1 M binary ethyleneimine and adjuvanted individually with 5% POLOYGEN™. The feline leukemia used for this combination was that prepared in EXAMPLE 3. Individually inactivated and adjuvanted components were combined in proportions adequate to produce a 1.0 mL dose volume. The five protective antigen components were all demonstrated to be immunogenically effective by testing in the specific ELISA tests as described in EXAMPLE 3. The feline rhinotracheitis component had an RP of 1.12 as compared to a vaccine with a value of 1.0 which protected 100% of cats in a severe vaccination/challenge test. The feline calicivirus component demonstrated an RP of 1.69 as compared to a vaccine with a value of 1.0 which protected 100% of cats in a severe vaccination/-challenge test. The feline panleukopenia virus showed an RP of 1.26 as compared to a vaccine with a value of 1.0 which protected 100% of cats in a severe vaccination/challenge test. The chlamydia component was tested for its protective capability in a cat vaccination/challenge test. It protected 100% of the vaccinated cats.

The five-way feline combination of this invention was compared to competitor products which are known to cause reactivity of the kind described using SDS-PAGE. FIG. 2 is a photograph of this gel which demonstrates the amounts of non-host albumin and other proteins in the various products. It should be noted that such electrophoretic techniques have been demonstrated to detect albumin at levels of 0.5 mg/mL in vaccines. Gel lanes are numbered from left to right with #1 being the farthest left lane and #10 being the farthest right lane. In FIG. 2, lanes 1, 2 and 4 are monovalent FeLV vaccines which were found to be highly reactive in the field. They contain a significant amount (>1.0 mg/mL) of non-host albumin which is detectable by a band at approximately 66,000 daltons. These vaccines caused systemic reactions of the type previously described, as well as death in a significant number of animals when tested in field safety trials similar to the trial described in EXAMPLE 2B. Lane 3 is a molecular weight marker which contains bands at 14.3, 20, 29, 34.8, 58.1 and 97 kilodaltons. Lane 5 is the vaccine made according to EXAMPLE 2A which produced no systemic reactions when tested for safety in the field trial described in EXAMPLE 2B. It contains a nondetectable level of non-host albumin. The band which appears at 70 kilodaltons is indicative of the presence of the gp70 antigenic component. Lane 6 is 5% bovine serum albumin (BSA) which serves as a non-host albumin control. Note that the gp70 band in lane 5 is slightly higher than the midpoint of this non-host albumin band. Lane 7 is a 5-way inactivated combination feline vaccine with the same components as mentioned above which is marketed by Fort Dodge Laboratories under the name FEL-O-VAXLV-K® IV. As mentioned previously, the Compendium of Veterinary Products indicates that systemic reactions have been associated with this vaccine. Lane 8 is a 5-way modified live/inactivated combination feline vaccine with the same components as mentioned above which is marketed by Solvay under the name ECLIPSE® 4+FeLV. This vaccine is also known to be reactive in cats. Lane 9 contains a 3-way modified live combination feline vaccine containing only feline rhinotracheitis feline calicivirus and feline panleukopenia which is marketed by Intervet under the name PROTEX®-3. This vaccine does not contain FeLV so there should be no gp70 present. Therefore, the band at 66 kilodaltons is non-host albumin. This vaccine, when combined with an inactivated and adjuvanted FeLV vaccine in the same vaccine regimen, caused systemic reactions in a study conducted in collaboration with the inventors. Lane 10 is a 3-way modified live combination feline vaccine containing feline rhinotracheitis, feline calicivirus and feline panleukopenia which contains no adjuvant and is marketed by Solvay under the name ECLIPSE®-3. It does not contain FeLV so it should show no bands between 60 and 70 kilodaltons. However, there is a faint band at approximately 66 kilodaltons indicating that this vaccine contains non-host albumin. It would be expected that this product, when used in a vaccine regimen with an adjuvanted vaccine would produce systemic reactions. It is obvious from this Figure that the FeLV 5-Way combination vaccine made according to this invention contains the least amount of non-host albumin of any vaccine containing the five components. It is also obvious that all of the reactive vaccines contain a marked band which represents non-host albumin at a concentration above 0.5 mg/mL.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making a vaccine for an animal species, wherein:
   the vaccine comprises an antigen, an adjuvant, and serum or albumin;
   and the process comprises:
   mixing the serum or albumin with the antigen to form a mixture of antigen and serum or albumin,
   lyophilizing the mixture of antigen and serum or albumin, and
   mixing the adjuvant with the mixture of antigen and serum or albumin, wherein said serum or albumin comprises serum or albumin obtained from said animal species.

* * * * *